US008834549B2

(12) United States Patent
Tarcha et al.

(10) Patent No.: US 8,834,549 B2
(45) Date of Patent: Sep. 16, 2014

(54) ONE-STEP PHOSPHORYLCHOLINE-LINKED POLYMER COATING AND DRUG LOADING OF STENT

(75) Inventors: Peter J. Tarcha, Lake Villa, IL (US); David Pecosky, Gurnee, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 13/305,881

(22) Filed: Nov. 29, 2011

(65) Prior Publication Data

US 2012/0071967 A1    Mar. 22, 2012

Related U.S. Application Data

(62) Division of application No. 11/753,731, filed on May 25, 2007, now Pat. No. 8,084,077.

(51) Int. Cl.
*A61F 2/06*    (2013.01)
*A61L 31/10*   (2006.01)
*A61L 31/16*   (2006.01)

(52) U.S. Cl.
CPC ........... *A61L 31/10* (2013.01); *A61L 2420/02* (2013.01); *A61F 2250/0067* (2013.01); *A61L 31/16* (2013.01); *A61L 2300/606* (2013.01)
USPC ......... 623/1.1; 427/2.24; 427/2.25; 623/1.15; 623/1.2; 623/1.42; 623/1.43

(58) Field of Classification Search
USPC .............. 623/1.1, 1.42; 427/2.24, 2.25, 427.1
See application file for complete search history.

(56) References Cited

U.S. PATENT DOCUMENTS

| | | | |
|---|---|---|---|
| 5,356,433 A * | 10/1994 | Rowland et al. | 424/422 |
| 6,248,811 B1 * | 6/2001 | Ottersbach et al. | 523/423 |
| 6,471,979 B2 | 10/2002 | New et al. | |
| 6,471,980 B2 | 10/2002 | Sirhan et al. | |
| 6,635,269 B1 | 10/2003 | Jennissen et al. | |
| 2003/0039689 A1 | 2/2003 | Chen et al. | |
| 2003/0125800 A1 * | 7/2003 | Shulze et al. | 623/1.15 |
| 2004/0185081 A1 * | 9/2004 | Verlee et al. | 424/423 |
| 2005/0013729 A1 * | 1/2005 | Brown-Skrobot et al. | 422/24 |
| 2005/0021152 A1 * | 1/2005 | Ogle et al. | 623/23.72 |
| 2008/0292778 A1 | 11/2008 | Tarcha et al. | |

FOREIGN PATENT DOCUMENTS

| | | |
|---|---|---|
| WO | WO0062830 | 10/2000 |
| WO | WO0065352 | 11/2000 |
| WO | WO0101957 | 1/2001 |
| WO | WO0156646 | 8/2001 |
| WO | WO02055121 | 7/2002 |
| WO | WO03011250 | 2/2003 |
| WO | WO03068289 | 8/2003 |
| WO | WO2004023985 | 3/2004 |

OTHER PUBLICATIONS

Lewis et al., "Crosslinkable coatings from phosphorylcholine-based polymers," Biomaterials. Jan. 2001;22(2):99-111.
Lewis et al., "Phosphorylcholine-based polymer coatings for stent drug delivery," J Mater Sci Mater Med. Oct.-Dec. 2001;12(10-12):865-70.
Lewis et al., "Analysis of a phosphorylcholine-based polymer coating on a coronary stent pre- and post-implantation," Biomaterials. Apr. 2002;23(7):1697-706.
Lewis et al., "Phosphorylcholine-coated stents," J Long Term Eff Med Implants. 2002;12(4):231-50.
Swanson et al., "Human internal mammary artery organ culture model of coronary stenting: a novel investigation of smooth muscle cell response to drug-eluting stents," Clin Sci (Lond). Oct. 2002;103(4):347-53.
Joung et al., "Estrogen release from metallic stent surface for the prevention of restenosis," J Control Release. Sep. 19, 2003;92(1-2):83-91.
Palmer et al., "Biological evaluation and drug delivery application of cationically modified phospholipid polymers," Biomaterials. Aug. 2004;25(19):4785-96.
Walter et al., "Local gene transfer of phVEGF-2 plasmid by gene-eluting stents: an alternative strategy for inhibition of restenosis," Circulation. Jul. 6, 2004;110(1):36-45. Epub Jun. 21, 2004.
U.S. Appl. No. 11/753,731, Non-final Office Action issued Nov. 26, 2010.
U.S. Appl. No. 11/753,731, Amendment and Response to non-final Office Action filed Mar. 25, 2011.
U.S. Appl. No. 11/753,731, Examiner Interview Summary Record issued May 12, 2011.
U.S. Appl. No. 11/753,731, Final Office Action issued May 26, 2011.
U.S. Appl. No. 11/753,731, Amendment after Final filed Aug. 4, 2011.
U.S. Appl. No. 11/753,731, Notice of Allowance issued Aug. 30, 2011.
U.S. Appl. No. 11/753,731, Issued Fee payment submitted Nov. 28, 2011.

* cited by examiner

*Primary Examiner* — Dah-Wei D Yuan
*Assistant Examiner* — Andrew Bowman
(74) *Attorney, Agent, or Firm* — Baker Botts L.L.P.

(57) ABSTRACT

A one step method for drug coating an interventional device is disclosed by mixing a drug with a phosphorylcholine-linked methacrylate polymer in a liquid and applying the mixture to an interventional device, such as a stent, in a single step.

26 Claims, No Drawings

ONE-STEP PHOSPHORYLCHOLINE-LINKED POLYMER COATING AND DRUG LOADING OF STENT

This application is a divisional of U.S. patent application Ser. No. 11/753,731, filed May 25, 2007 now U.S. Pat. No. 8,084,077, the disclosure of which is incorporated herein by reference in its entireties to the extent permitted by law.

BACKGROUND

1. Field of Invention

The present invention relates to a one-step method for loading a drug coating onto an interventional device. Particularly, the present invention is directed to a method of mixing a drug with a phosphorylcholine-linked methacrylate polymer in a liquid and applying the mixture to an interventional device, such as a stent, in a single step.

2. Description of Related Art

Cardiovascular disease is prevalent in the United States and in other parts of the world. One manifestation of cardiovascular disease is atherosclerosis, which is the buildup of plaque (or fatty deposits) on the walls of blood vessels, such as coronary arteries. This buildup of plaque can grow large enough to reduce blood flow through the blood vessel. Serious damage results when an area of plaque ruptures and forms a clot, which travels to another part of the body. If the blood vessels that feed the heart are blocked, a heart attack results. If the blood vessels to the brain are blocked, a stroke results. Thus, atherosclerosis can be fatal for some people.

Percutaneous transluminal coronary angioplasty (PTCA) is a procedure for treating atherosclerosis. Angioplasty is the mechanical widening of an obstructed blood vessel. This procedure generally entails introducing a catheter assembly into the cardiovascular system of a patient via the brachial or femoral artery. Once introduced, the catheter assembly is advanced through the coronary vasculature until the balloon portion of the catheter assembly is positioned across an occlusive lesion. When positioned across the lesion, the balloon is inflated to a size sufficient to radially compress the plaque against the vessel wall. Subsequently, the balloon is deflated to allow the catheter assembly to be withdrawn from the vasculature of the patient.

While PTCA is widely used, it suffers from two unique problems. First, the blood vessel may suffer acute occlusion immediately after or within the initial hours after the dilation procedure. Such occlusion is referred to as "abrupt closure." Abrupt closure occurs in approximately five percent of cases in which PTCA is employed. The primary mechanisms of abrupt closures are believed to be elastic recoil, arterial dissection and/or thrombosis. The second problem associated with this procedure is the re-narrowing of an artery after an initially successful angioplasty. This re-narrowing is referred to as "restenosis," which among other things, typically occurs within the first six months after angioplasty. Restenosis is believed to be due to the proliferation and migration of cellular components from the arterial wall, as well as through geometric changes in the arterial wall referred to as "remodeling."

To overcome some of the drawbacks of angioplany, such as reducing occlusion of the artery, thrombosis formation and/or restenosis, it is known to implant an expandable interventional device or prosthesis to maintain patency. One example is a stent. A stent is a mesh tubular member used to prop open a lumen. The stent is collapsed onto a catheter or stent delivery device and travels to the area of blockage while secured onto the catheter. The stent is positioned across the blockage or lesion and radially expands to prop open the blood vessel.

To better effectuate the treatment of atherosclerosis and other cardiovascular diseases, it is beneficial to load an intraluminal device or prosthesis with one or more therapeutic agents, such as antiproliferatives, for delivery to a lumen. One commonly applied technique for the local delivery of a drug to a stent, for example, is through the use of a polymeric carrier coated onto the surface of a stent, as disclosed in Berg et al., U.S. Pat. No. 5,464,650, the disclosure of which is incorporated herein by reference. Berg's method of loading drug onto the stent, however, requires multiple repetitive coating steps to achieve uniformity and control over the amount of therapeutic substance to be applied to the stent. Furthermore, Berg requires an evaporation step so that the coating of the final product includes the drug and polymer but little or no residual solvent.

Although conventional methods and products such as those taught by Berg generally have been considered satisfactory for their intended purpose. Such conventional methods are inefficient and costly due to the requirement of separate, multiple coating and time for sufficient evaporation. Additionally, each additional step of such conventional processes require additional manipulation of the stent being coated. Because stents are, by their very nature, fragile devices, additional manipulation increases the risk of physical damage and contamination of the stent. There thus remains a need for an efficient and economic method and system for loading a drug into a polymer coating for application to a stent with a minimum amount of manipulation of the stent or similar device and to allow for uniform distribution of the polymer coating.

SUMMARY OF THE INVENTION

To achieve these and other advantages the invention, an efficient method of making a drug eluting interventional device that requires less steps to achieve a device loaded with therapeutic agent, is provided. The method is not only more efficient because it requires less steps and material to achieve a drug eluting interventional device, excessive manipulation of the interventional device during the process is not necessary because the device can be sufficiently coated in one step.

The method comprises providing an interventional device having a bare surface and mixing at least one therapeutic agent and at least one polymer in a liquid to form a mixture. The mixture is applied to a portion of the bare surface of the interventional device to form a coating. Advantageously, no base coating is applied to the stent.

The polymer component of the mixture may be a crosslinkable polymer, such as phosphorylcholine-linked methacrylate polymer. The polymer, may further include a trimethoxysilane functional group. The polymer or polymers and at least one therapeutic agent may be mixed using ethanol as the liquid.

The therapeutic agent component of the mixture may be a variety of therapeutic agents. The term "therapeutic agent" as used herein, refers to any compound, mixture of compounds, or composition of matter consisting of a compound, which produces a therapeutic or useful result. For example and as will be discussed below. The therapeutic agent can be a polymer, a marker, such as a radiopaque dye or particles, or can be a drug, including pharmaceutical agents, or an agent including inorganic or organic drugs without limitation. The therapeutic agent can be in various forms, such as uncharged molecules, components of molecular complexes, pharmacologically acceptable salts such as hydrochloride, hydrobromide, sulfate, laurate, palmitate, phosphate, nitrate, borate, acetate, maleate, tartrate, oleate, and salicylate.

The coated interventional device may include about 10 to about 13 micrograms of therapeutic agent along a linear millimeter of the length of the device or as needed for the desired end product. The coating may include 30% by weight of the therapeutic agent or agents relative to the polymer or as needed for the desired end product. Also, the coating may include a uniform matrix of therapeutic agent and polymer. Any number of drug-to-polymer ratios may be used depending on the desired properties of drug release and polymer functional attributes such as flexibility, biodegradability, adhesiveness, etc.

A variety of methods can be utilized to apply the mixture to the bare surface of the interventional device. For example, spraying, dipping, jetting, or any other coating application techniques can be used.

The mixture can be uniformly applied to at least a portion of the interventional. In this regarding the entire surface of the interventional device can be coated or only a section of the interventional device can be coated if desired. Also, the therapeutic agent or agents may be uniformly distributed in the coating, or layered or otherwise disbursed or dissolved in or on the coating or coatings. The coating may have a thickness of about 5 to about 6 microns.

The method may include curing the coated interventional device, such as by heating. If desired, the method may include applying an overcoating to at least a portion of the stent.

The coated stent may be mounted to a delivery device and sterilized. The sterilization of the coating stent may include irradiating the coating. The coated stent may be dried before being sterilized or otherwise processed as desired. Additionally, the sterilizing step may facilitate crosslinking of the polymer coating. The sterilizing step may include exposing the coated stent to at least one cycle of ethylene oxide or heat.

The interventional device can be, for example, a self-expandable or balloon-expandable stent, a graft, filter, or balloon.

It is to be understood that both the foregoing general description and the following detailed description are exemplary and are intended to provide further explanation of the invention claimed.

DETAILED DESCRIPTION

Reference will now be made in detail to the present embodiments of the invention. The method and corresponding steps of the invention will be described in conjunction with the detailed description of the system.

The methods and products presented in this disclosure may be used for achieving an eluting interventional device, such as a drug eluting stent or balloon. The present invention is particularly suited for preparing drug eluting interventional devices in which the drug is loaded onto the interventional device in one step.

The method generally includes mixing at least one therapeutic agent and at least one polymer in a liquid to form a mixture. The mixture is applied to a bare surface of the interventional device. The application step may include selectively coating a surface of the interventional device. In this regard, the entire surface of the interventional device can be coated or alternatively, only predetermined selections of the interventional device can be coated. In this manner, a mask can be used if a selected coating pattern is desired. The application step can include coating the surface of the interventional device by various techniques, such as spray coating, dipping, or jetting, or other art-known application techniques.

In one embodiment, the mixture includes a crosslinkable polymer, such as a phosphorylcholine-linked methacrylate polymer. The phosphorylcholine-linked polymer can include one or more trimethoxysilane functional groups. It is believed that the trimethoxysilane functional group allows crosslinking of the polymer. Alternatively, a linear phosphorylcholine polymer can be used. The polymer is mixed in a liquid, such as ethanol.

Additionally, a therapeutic agent is mixed in the liquid with the polymer such that a polymer-therapeutic agent liquid mixture is formed. In one embodiment, the therapeutic agent and the polymer is mixed in a common solvent, such as ethanol. The mixture is applied to a surface of the interventional device in one step to form a therapeutic agent loaded coating on the interventional device. Advantageously, repetitive coating steps are not required to achieve a drug eluting interventional device.

The coating layer can be applied to the surface of the interventional device such that a thickness of about 5 to 6 microns in thickness is achieved. If desired, an overcoating layer may be applied to the coating layer. For example, the overcoating layer can be an uncrosslinked phosphorylcholine polymer.

The method can further include a curing step during which the coated interventional device is cured. In one embodiment, the curing included heat curing the coated interventional device. In one example, a mixture of ABT-578 and phosphorylcholine-linked methacrylate polymer is applied to the a stent. The coated stent is cured by heating at about 70 degrees Celsius for about four hours. Importantly, the drug is stable and does not substantially degrade during the heat curing step.

The method can further include a sterilizing step. In this regard, the interventional device may be mounted to a delivery device and sterilized by irradiating the coated interventional device. The sterilizing may include exposing the coated interventional device to at least one cycle of ethylene oxide.

In an embodiment of the present invention, a stent is loaded with therapeutic agent such as ABT-578 with polymer, overcoated with non-crosslinked phosphorylcholine polymer, and mounted on a balloon. The stent is then subjected to ethylene oxide (ETO) sterilization. ETO sterilization is a high humidity (>40% RH) process done at room or elevated temperature (20-60 degrees C.). The ETO cycle results in crosslinking of the overcoating phosphorylcholine polymer.

A variety of therapeutic agents are suitable for coating the interventional device. Moreover, a combination of therapeutic agents can be used. For example, the therapeutic agent may be rapamycin or a derivative or analog thereof.

As noted above, the interventional device is at least partially loaded with therapeutic agent. In an embodiment of the invention, at least one therapeutic agent can be selected from but not limited to anti-proliferative, anti-inflammatory, anti-neoplastic, antiplatelet, anti-coagulant, anti-fibrin, anti-thrombotic, antimitotic, antibiotic, antiallergic and antioxidant compounds. For example, the therapeutic agent can be a pharmaceutical agent or drug such as rapamycin or a derivative or analog thereof. According to the McGraw-Hill Dictionary of Scientific and Technical Terms, Fifth Edition, an analog is "[a] compound whose structure is similar to that of another compound but whose composition differs by one element," and a derivative is "a substance that is made from another substance." These definitions are adopted throughout this document.

The therapeutic agent may be a synthetic inorganic or organic compound, a protein, a peptide, a polysaccharides and other sugars, a lipid, DNA and RNA nucleic acid sequences, an antisense oligonucleotide, an antibodies, a receptor ligands, an enzyme, an adhesion peptide, a blood clot agent including streptokinase and tissue plasminogen activator, an antigen, a hormone, a growth factor, a ribozyme, a retroviral vector, an anti-proliferative agent including rapamycin (sirolimus), 40-O-(2-hydroxyethyl)rapamycin (everolimus), 40-O-(3-hydroxypropyl)rapamycin, 40-O-(2-hydroxyethyoxy)ethylrapamycin, 40-O-tetrazolylrapamycin (zotarolimus, ABT-578), paclitaxel, docetaxel, methotrexate, azathioprine, vincristine, vinblastine, fluorouracil, doxorubicin hydrochloride, and mitomycin, an antiplatelet compound, an anticoagulant, an antifibrin, an antithrombins including sodium heparin, a low molecular weight heparin, a heparinoid, hirudin, argatroban, forskolin, vapiprost, prostacyclin, a prostacyclin analogue, dextran, D-phe-pro-arg-chloromethylketone (synthetic antithrombin), dipyridamole, glycoprotein IIb/IIIa platelet membrane receptor antagonist antibody, recombinant hirudin, a thrombin inhibitor including Angiomax®, a calcium channel blocker including nifedipine, colchicine, a fibroblast growth factor (FGF) antagonist, fish oil (omega 3-fatty acid), a histamine antagonist, lovastatin, a monoclonal antibodies, nitroprusside, a phosphodiesterase inhibitor, a prostaglandin inhibitor, suramin, a serotonin blocker, a steroid, a thioprotease inhibitor, triazolopyrimidine, a nitric oxide or nitric oxide donor, a super oxide dismutase, a super oxide dismutase mimetic, estradiol, an anticancer agent, a dietary supplement including vitamins, an anti-inflammatory agent including aspirin, tacrolimus, dexamethasone and clobetasol, a cytostatic substance including angiopeptin, an angiotensin converting enzyme inhibitor including captopril, cilazapril or lisinopril, an antiallergic agent including permirolast potassium, alpha-interferon, bioactive RGD, and genetically engineered epithelial cells. Other therapeutic agents which are currently available or that may be developed in the future for use with implantable medical devices may likewise be used and all are within the scope of this invention.

Examples of such antithrombotics, anticoagulants, antiplatelet agents, and thrombolytics include sodium heparin, low molecular weight heparins, heparinoids, hirudin, argatroban, forskolin, vapriprost, prostacyclin and prostacylin analogues, dextran, D-phe-pro-arg-chlorometh-ylketone (synthetic antithrombin), dipyridamole, glycoprotein IIb/IIIa (platelet membrane receptor antagonist antibody), recombinant hirudin, and thrombin inhibitors such as Angiomax®, from Biogen, Inc., Cambridge, Mass.; and thrombolytic agents, such as urokinase, e.g., Abbokinase® from Abbott Laboratories Inc., North Chicago, Ill., recombinant urokinase and pro-urokinase from Abbott Laboratories Inc., tissue plasminogen activator (Alteplase® from Genentech, South San Francisco, Calif. and tenecteplase (TNK-tPA).

Examples of such cytostatic or antiproliferative agents include rapamycin and its analogs such as everolimus, ABT-578, i.e., 3S,6R,7E,9R,10R,12R,14S,15E,17E,19E,21S,23S,26R,27R,34aS)-9,10,12,13,14,21,22,23,24,25,26,27,32,33,34,34a-Hexadecahydro-9,27-dihydroxy-3-[(1R)-2-[(-1S,3R,4R)-3-methoxy-4-tetrazol-1-yl)cyclohexyl]-1-methylethyl]-10,21-dimet-hoxy-6,8,12,14,20,26-hexamethyl-23,27-epoxy-3H-pyrido[2,1-c][1,4]oxaazacyclohentriacontine-1,5,11,28,29(4H,6H,31H)-pentone; 23,27-Epoxy-3H pyrido[2,1-c][1,4]oxaazacyclohentriacontine-1,5,11,28,29(4H,6H,31H)-pentone, which is disclosed in U.S. Pat. No. 6,015,815, U.S. Pat. No. 6,329,386, U.S. Publication 2003/129215, filed on Sep. 6, 2002, and U.S. Publication 2002/123505, filed Sep. 10, 2001, the disclosures of which are each incorporated herein by reference thereto, tacrolimus and pimecrolimus, angiopeptin, angiotensin converting enzyme inhibitors such as captopril, e.g, Capoten® and Capozide® from Bristol-Myers Squibb Co., Stamford, Conn., cilazapril or lisinopril, e.g., Prinivil® and Prinzide® from Merck & Co., Inc., Whitehouse Station, N.J.; calcium channel blockers such as nifedipine, amlodipine, cilnidipine, lercanidipine, benidipine, trifluperazine, diltiazem and verapamil, fibroblast growth factor antagonists, fish oil (omega 3-fatty acid), histamine antagonists, lovastatin, e.g. Mevacor® from Merck & Co., Inc., Whitehouse Station, N.J. In addition, topoisomerase inhibitors such as etoposide and topotecan, as well as antiestrogens such as tamoxifen may be used.

Examples of such anti-inflammatories include colchicine and glucocorticoids such as betamethasone, cortisone, dexamethasone, budesonide, prednisolone, methylprednisolone and hydrocortisone. Non-steroidal anti-inflammatory agents include flurbiprofen, ibuprofen, ketoprofen, fenoprofen, naproxen, diclofenac, diflunisal, acetaminophen, indomethacin, sulindac, etodolac, diclofenac, ketorolac, meclofenamic acid, piroxicam and phenylbutazone.

Examples of such antineoplastics include alkylating agents such as altretamine, bendamucine, carboplatin, carmustine, cisplatin, cyclophosphamide, fotemustine, ifosfamide, lomustine, nimustine, prednimustine, and treosulfin, antimitotics such as vincristine, vinblastine, paclitaxel, e.g., TAXOL® by Bristol-Myers Squibb Co., Stamford, Conn., docetaxel, e.g., Taxotere® from Aventis S.A., Frankfort, Germany, antimetabolites such as methotrexate, mercaptopurine, pentostatin, trimetrexate, gemcitabine, azathioprine, and fluorouracil, and antibiotics such as doxorubicin hydrochloride, e.g., Adriamycin® from Pharmacia & Upjohn, Peapack, N.J., and mitomycin, e.g., Mutamycin® from Bristol-Myers Squibb Co., Stamford, Conn., agents that promote endothelial cell recovery such as Estradiol.

A therapeutic agent that is water insoluble can be used in a form that is a water-soluble derivative thereof to effectively serve as a solute, and on its release from the device, is converted by enzymes, hydrolyzed by body pH, or metabolic processes to a biologically active form. Additionally, the agents or drug formulations can have various known forms such as solutions, dispersions, pastes, particles, granules, emulsions, suspensions and powders. The drug or agent may or may not be mixed with polymer or a liquid as desired.

While the foregoing therapeutic agents are known for their preventive and treatment properties, the substances or agents are provided by way of example and are not meant to be limiting. Further, other therapeutic agents that are currently available or may be developed are equally applicable for use with the present invention.

If desired or necessary, the therapeutic agent can include a binder to carry, load, or allow sustained release of an agent, such as but not limited to a suitable polymer or similar carrier. The term "polymer" is intended to include a product of a polymerization reaction inclusive of homopolymers, copolymers, terpolymers, etc., whether natural or synthetic, including random, alternating, block, graft, branched, cross-linked, blends, compositions of blends and variations thereof. The polymer may be in true solution, saturated, or suspended as particles or supersaturated in the therapeutic agent. The polymer can be biocompatible, or biodegradable.

For purpose of illustration and not limitation, the polymeric material may include phosphorylcholine linked macromolecules, such as a macromolecule containing pendant phosphorylcholine groups such as poly($MPC_w$:$LMA_x$:$HPMA_y$:$TSMA_z$), where MPC is 2-methacryoyloxyethylphosphorylcholine, LMA is lauryl methacrylate, HPMA is hydroxypropyl methacrylate and TSMA is trimethoxysilylpropyl methacrylate, and w, x, y, and z are molar ratios of the monomers used in the feed. These values are typically 23, 47, 25, and 5, respectively, but they are not necessarily the ratios that exist in the finished polymer. The polymer is herein referred to generally as "PC polymer."

The therapeutic agent can include a liquid. The liquid can be any single solvent or a combination of solvents. For purpose of illustration and not limitation, examples of suitable solvents include water, aliphatic hydrocarbons, aromatic hydrocarbons, alcohols, ketones, dimethyl sulfoxide, tetrahydrofuran, dihydrofuran, dimethylacetamide, acetates, and combinations thereof. Preferably, the solvent is ethanol. More preferably, the solvent is isobutanol. Additionally, in another aspect of the invention, multiple therapeutic agents are dissolved or dispersed in the same solvent. For purpose of illustration and not for limitation, dexamethasone, estradiol, and paclitaxel are dissolved in isobutanol. Alternatively, dexamethasone, estradiol, and paclitaxel are dissolved in ethanol. In yet another example, dexamethasone, estradiol, and ABT-578, i.e., the rapamycin analog, 3S,6R,7E,9R,10R,12R,14S, 15E,17E,-19E,21S,23-S,26R,27R,34aS)9,10,12,13,14,21, 22,23,24,25,26,27,32,33,34,34a-Hexadecahydro-9,27-dihydroxy-3-[(1R)-2-[(1S,3R,4R)-3-methoxy-4-tetrazol-1-yl)cyclohexyl]-1-methylethyl]-10,21-dimethoxy-6,8,12,14, 20,26-hexamethyl-2-3,27-epoxy-3H-pyrido[2,1-c][1,4] oxaazacyclohentriacontine-1,5,11,28,29(4H,6H,31H)-pentone; 23,27-Epoxy-3H-pyrido[2,1-c][1,4] oxaazacyclohentriacontin-e-1,5,11,28,29(4H,6H,31H)-pentone, are dissolved together in one solvent. Preferably, the solvent is ethanol or isobutanol. Ethanol is more preferable for spray coating of the mixture and isobutanol is more preferable for jetting of the mixture.

Additionally, the therapeutic agent includes any of the aforementioned drugs, agents, polymers, and liquids either alone or in combination.

As used herein "interventional device" refers broadly to any device suitable for intraluminal delivery or implantation. For purposes of illustration and not limitation, examples of such interventional devices include stents, grafts, stent-grafts, filters, balloons, and the like. As is known in the art, such devices may comprise one or more prostheses, each having a first cross-sectional dimension or profile for the purpose of delivery and a second cross-sectional dimension or profile after deployment. Each prosthesis may be deployed by known mechanical techniques such as balloon expansion deployment techniques, or by electrical or thermal actuation, or self-expansion deployment techniques, as well known in the art.

The stent can be in an expanded or unexpanded state during the loading of therapeutic agent. The underlying structure of the stent can be virtually any structural design and the interventional device can be composed any suitable material such as, but not limited to, stainless steel, "MP35N," "MP20N," elastinite (Nitinol), tantalum, nickel-titanium alloy, platinum-iridium alloy, gold, magnesium, polymer, ceramic, tissue, or combinations thereof. "MP35N" and "MP20N" are understood to be trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium and 10% molybdenum. The stent can be made from bioabsorbable or biostable polymers. In some embodiments, the surface of the interventional device can include one or more reservoirs or cavities formed therein, as described further below.

The stent can be fabricated utilizing any number of methods known in the art. For example, the stent can be fabricated from a hollow or formed tube that is machined using lasers, electric discharge milling, chemical etching or other known techniques. Alternatively, the stent can be fabricated from a sheet that is rolled into a tubular member, or formed of a wire or filament construction as known in the art. Examples of such for purpose of illustration include U.S. Pat. No. 4,733,665 to Palmaz; U.S. Pat. No. 6,106,548 to Roubin et al.; U.S. Pat. No. 4,580,568 to Gianturco; U.S. Pat. No. 5,755,771 to Penn et al.; and U.S. Pat. No. 6,033,434 to Borghi, all of which are incorporated herein by reference.

In another embodiment, the interventional device can be a balloon. The balloon can be formed from a polymer tubular member. The polymer can be selected from a variety of materials including nylon, Pebax®, Hytrel® or a blend thereof. Additionally, other materials can be used if desired.

Example 1

Uncrosslinked phosphorylcholine polymer provided as a dry powder. 1.0 gram of phosphorylcholine polymer powder was placed into each of three 3.5"×8" Tyvec pouches designed for use as containers in radiation and ethylene oxide (ETO) sterilization experiments. The first pouch was subjected to one complete ETO cycle, including preconditioning. The second pouch was subjected to two ETO cycles, and the third pouch was subjected to three complete cycles. Subsequently, the samples were transferred to glass vials and placed in refrigerated storage. Each cycle involved preconditioning of the sample before the introduction of ETO for approximately 12 hours at 46 degrees Celsius under a relative humidity of 65%. The sample experiences ETO at 6 psi for about 5 hours at 46-50 degrees Celsius.

Example 2

After the ETO sterilization process the sample that had undergone three cycles was prepared for NMR analysis. A weight of 20 mg were dissolved in 1.6 ml of deuterated chloroform containing TMS as a reference, by shaking on a wrist action shaker overnight. The presence of insolubles was noted in the sample after the solvent dissolution by a cloudy layer that creamed to the surface. The cloudy layer had a particulate consistency like silica gel swollen by a solvent, and was not suitable for solution-state NMR. The clear bottom layer was used for analysis. Samples that were not ETO-sterilized dissolved completely under these conditions demonstrating that the ETO process caused insolubles to form, due to crosslinking of the silane functionalities.

Example 3

50 mg samples of phosphorylcholine polymer that had been subjected to 0, 1, 2, and 3 ETO cycles were separately dissolved in 1 ml of chloroform and shaken overnight. After shaking, the samples were allowed to stand. Cloudy layers creamed to the surface of the treated samples. The untreated sample was totally clear. The sample that was subjected to 1 cycle had a cloudy layer that was of greater volume than that of the 2 and 3 cycle samples, but slightly less concentrated as evidenced by less intense visible light scattering. In duplicate, additional 50 mg samples from each of the runs corresponding to 1, 2, and 3 ETO cycles were dissolved in 1 ml of chloroform and shaken overnight. Once again the insoluble material creamed to the top. The bottom solvent layer was removed and the insolubles were extracted three additional times with 2 ml aliquots of ethanol. In ethanol the insolubles settled to the bottom of the vials and the clear top layers were removed during the extraction process. After the third extraction, the samples were transferred completely as a suspension in ethanol to pre-weighed scintillation vials and dried in an oven overnight at 70 degrees Celsius. Based on the weights of the vials it was found that 1, 2, and 3 ETO cycles caused 67%, 75%, and 83% respectively, of the phosphorylcholine material to become insoluble particulates.

Example 4

The sample that was subjected to three ETO sterilization cycles was used for the spectroscopic analysis because any changes or by-products due to the sterilization cycles would be magnified to the greatest extent in this sample. Control samples were unmodified phosphorylcholine polymer that never experienced preconditioning or ETO. The NMR results generated spectra that were consistent with the known structure of the phosphorylcholine polymer in both the native unsterilized polymer and the ETO processed polymer. Chemical changes to the polymer or residuals as a result of the ETO sterilization process were not evident in any of the spectra run on ETO processed material. This is not surprising because the crosslinking monomer is present at only 5% and silicone bond formation results in changes 2 bonds away from the nearest carbon, a longer range and less sensitive effect in NMR.

Example 5

The infrared analysis indicated that the spectra, run in duplicate, obtained from the ETO treated sample are very similar to the spectra obtained from the control sample. Small differences were noted in the 800-900 cm-1 region.

Example 6

Phosphorylcholine polymer from the same batch as was used for the ETO process experiments was used to determine the effects of heat curing. Three glass scintillation vials were flamed and cooled to eliminate moisture and weighed on an analytical balance. Approximately 200 mg of phosphorylcholine polymer was added to each vial and the vials were reweighed. A volume of 1 ml of ethanol was added to each vial and the contents shaken on a wrist action shaker for 20 minutes to form a solution. The caps of the vials were then removed and the ethanol allowed to evaporate overnight. A film of polymer was evident on the bottom of the vials. The vials were put into an oven at 70 degrees Celsius for 4.25 hours, to approximate the typical heat-curing conditions previously used with drug-eluting stent (DES) preparation. The vials were then removed and 5 ml of ethanol was added, and then shaken for 30 minutes. The presence of insolubles was not evident. The extracts were removed and placed in pre-weighed vials and the solvent was evaporated at 70 degrees Celsius to visible dryness followed by 111 degrees Celsius for 2 hours to remove all traces of ethanol. Reweighing the vials containing the extracts indicated that 89, 60, and 73% respectively of the samples had gone into the extraction solvent after the first extraction. The data indicated that 1 ETO cycle produced more insolubles than the currently used heat-curing due to more complete crosslinking.

Example 7

To 88 grams (111 ml) of ethanol was added 4.0 grams of ABT-578 and 8.0 grams of phosphorylcholine polymer. The mixture was mixed to form a stock solution. A 15 mm coronary stent requires 150 micrograms of ABT-578 and therefore needed to obtain 6.33 microliters of solution to give the proper dosage of drug. By weighting, the stent needed to obtain 450 micrograms of solids. If a reagent jetter is used to dispense the drug and the process is 75% efficient and the droplet size is 50 microns, the jetter needs to be programmed to jet 129,052 drops per stent. After the required amount of solution is applied to the stent and the stent is dried, it is mounted on a balloon and subjected to 1 ETO sterilization cycle to complete the process.

Example 8

Weighed 129 mg of ABT-578, a rapamycin derivative and 280 mg of phosphorylcholine-linked methacrylate terpolymer PC1036 and dissolved them in 10 ml of 100% by shaking overnight protected from light. The solution was filtered through a 0.45 micron Teflon filter and the solution was added to the syringe reservoir of a semi-automated spray atomization gun coupled to a lathe-like device designed to hold stents, rotate them and translate them linearly in front of the spray gun. The equipment was programmed to spray enough solution in order to obtain about 10 micrograms of drug per linear mm of stent length, taking into account the losses of solution due to lack of contact with the stent as it is sprayed. After spraying, the stents were allowed to dry in air, followed by packaging them individually in glass vials sealed with an ETO permeable Tyvec membrane. The samples were sent out for ETO sterilization by one or three complete cycles.

Example 9

Analysis was done of the total drug level from 5 stents that underwent 1 ETO cycle and 5 stents that underwent 3 ETO cycles using standard extraction and HPLC analysis. It was found that the amount of drug in stents that underwent 3 cycles was approximately the same as in those that underwent 1 cycle, an indication that the drug was stable to 3 ETO cycles. The 15 mm and 18 mm stents had an average dosage of ABT-578 of 191 and 188 micrograms respectively with an 18% standard deviation.

Example 10

Ten ABT-578 DES samples were tested. Five of the stents experienced one ETO sterilization cycle while the remaining five stents completed three ETO cycles, including three preconditioning steps. The stents were spray loaded with phosphorylcholine and ABT-578 at 32% drug relative to the phosphorylcholine (w/w). Twenty-four hour release curves were requested for the samples using a 1% Solutol media. All of the samples had remaining ABT-578 on the stents at the 24 hour time point. The samples that had finished only one ETO cycle eluted faster (approximately 80% at 24 hours) than the three cycle ETO samples (approximately 70% at 24 hours), suggesting that the 3 cycle samples retained the drug on the stent more robustly over the 24 hour time period.

Example 11

Stents were observed under a stereomicroscope after dissolution and after extraction with 50% acetonitrile. Detachment of the coating during this dissolution process appears evident by the presence of filaments that coexist with and are intertwined in the struts after the dissolution period ends. These filaments are not present at the start of the experiment and the stent looks quite cosmetically pleasing. After extraction with 100% acetonitrile, no filaments were evident indicating that they detached completely.

Example 12

The example was done to compare the delamination potential of both the Zomaxx DES and the stents coated in one step by the methods and with the compositions of the present invention. 224 ml of 100 pig serum was placed into centrifuge tubes and spun at 3500 RPM for 10 minutes. A cloudiness creamed to the surface along with a few large flakes of white material. The extraneous white materials and cloudy layers were removed by decanting with the assistance of a spatula during decantation. The bottom layers in the tubes were retained for a total volume of 170 ml. A volume of 0.8 ml of concentrated sodium azide solution in distilled water was added to the serum to give it a concentration of 0.01% to prevent microbial growth.

Two Zomaxx drug eluting coronary stents of 3.0 mm×18 mm were expanded and freed from their balloons. They were placed in 20 ml scintillation vials. They were photographed under the stereoscope and were found to exhibit no evidence of coating detachment. 10 ml of the pig serum was added to each vial and they were placed in a shaker (air heated incubator, Labline, 27 degrees C., 100 RPM) for 3 days. The stents rested gently on the bottom of the vials. After the incubation, the stents were rinsed once with PBS to prevent protein precipitation and remove loosely adhering protein and rinsed a second time with distilled water. No obvious evidence of coating detachment was seen.

The same process was performed on two stents that had been coated by the one step process of this invention. One stent had experience 1 ETO cycle and the other stent had experienced 3 ETO cycles. After the 3 day incubation, the stents were examined under Reflectance infrared spectroscopy, and it was confirmed that the coatings did not detach from the Zomaxx or the one-step stents.

It will be apparent to those skilled in the art that various modifications and variations can be made in the method and system of the present invention without departing from the spirit or scope of the invention. Thus, it is intended that the present invention include modifications and variations that are within the scope of the appended claims and their equivalents.

What is claimed is:

1. A drug eluting interventional device produced by a method comprising:
   providing an interventional device having a bare surface;
   mixing at least one therapeutic agent and at least one polymer in a solvent to form a mixture, wherein the at least one polymer includes phosphorylcholine;
   applying the mixture to at least a portion of the bare surface of the interventional device to form a coating thereon, wherein no base coating is applied to the surface of the interventional device; and
   crosslinking the at least one polymer by sterilizing the coated interventional device, wherein crosslinking the at least one polymer comprises exposing the coated interventional device to multiple complete cycles of ethylene oxide sterilization, and wherein crosslinking the at least one polymer increases retention of the at least one therapeutic agent on the interventional device as compared to a substantially identical interventional device subject to crosslinking of the at least one polymer by exposure to a single complete cycle of ethylene oxide sterilization.

2. The drug eluting interventional device of claim 1, wherein the coated interventional device is exposed to three complete cycles of ethylene oxide sterilization.

3. The drug eluting interventional device of claim 1, wherein the mixture is applied to at least a portion of the bare surface of the interventional device by spraying, dipping or jetting techniques.

4. The drug eluting interventional device of claim 1, wherein the at least one polymer is a phosphorylcholine-linked methacrylate polymer.

5. The drug eluting interventional device of claim 4, wherein the at least one polymer comprises a trimethoxysilane functional group.

6. The drug eluting interventional device of claim 1, wherein the solvent is ethanol.

7. The drug eluting interventional device of claim 1, wherein the mixture is uniformly applied to at least a portion of the surface of the interventional device.

8. The drug eluting interventional device of claim 1, wherein the at least one therapeutic agent is uniformly distributed in the coating.

9. The drug eluting interventional device of claim 1, wherein the coating has a thickness of about 5 to about 6 microns.

10. The drug eluting interventional device of claim 1, wherein the method further comprises curing the coated interventional device.

11. The drug eluting interventional device of claim 10, wherein curing the coated interventional device comprises heating the coated interventional device at about 70° C. for about four hours.

12. The drug eluting interventional device of claim 1, wherein the method further comprises applying an overcoating to at least a portion of the coated interventional device.

13. The drug eluting interventional device of claim 1, wherein sterilizing the coated interventional device comprises irradiating the coating.

14. The drug eluting interventional device of claim 1, wherein the interventional device is a stent.

15. The drug eluting interventional device of claim 14, wherein the stent is a self-expanding or balloon expandable stent.

16. A drug eluting interventional device produced by a method comprising:
   providing an interventional device having an unactivated and bare surface;
   mixing at least one therapeutic agent and a phosphorylcholine polymer in a solvent to form a solution;
   applying the solution to at least a portion of the unactivated and bare surface of the interventional device to form a coating thereon, wherein no base coating is applied to the interventional device; and
   crosslinking the phosphorylcholine polymer by sterilizing the coated interventional device, wherein crosslinking the phosphorylcholine polymer comprises exposing the coated interventional device to multiple complete cycles of ethylene oxide sterilization, and wherein crosslinking the phosphorylcholine polymer increases retention of the at least one therapeutic agent on the interventional device as compared to a substantially identical interventional device subject to crosslinking of the phosphorylcholine polymer by exposure to a single complete cycle of ethylene oxide sterilization.

17. The drug eluting interventional device of claim 16, wherein the coated interventional device is exposed to three complete cycles of ethylene oxide sterilization.

18. The drug eluting interventional device of claim 16, wherein applying the solution to at least a portion of the unactivated and bare surface of the interventional device comprises spraying, dipping, jetting, syringe coating, or a combination thereof.

19. The drug eluting interventional device of claim 16, wherein the coated interventional device is dried prior to sterilizing the coated interventional device.

20. The drug eluting interventional device of claim 16, wherein the phosphorylcholine polymer comprises a trimethyoxysilane functional group.

21. The drug eluting interventional device of claim 16, wherein the at least one therapeutic agent is rapamycin or a derivative or analog thereof.

22. The drug eluting interventional device of claim 16, wherein the coated interventional device comprises about 10 to about 13 micrograms of the at least one therapeutic agent along a linear millimeter length of the coated interventional device.

23. The drug eluting interventional device of claim 16, wherein the coating comprises 30% by weight of the at least one therapeutic agent relative to the phosphorylcholine polymer.

24. The drug eluting interventional device of claim 16, wherein the coating comprises a uniform matrix of the at least one therapeutic agent and the phosphorylcholine polymer.

25. The drug eluting interventional device of claim 16, wherein the interventional device is a stent.

26. The drug eluting interventional device of claim 25, wherein the stunt is a self-expanding or balloon expandable stent.

* * * * *